US012715832B2

(12) United States Patent
Mei et al.

(10) Patent No.: US 12,715,832 B2
(45) Date of Patent: Aug. 25, 2026

(54) CO-CRYSTAL OF COENZYME QH AND NICOTINAMIDE, PREPARATION METHOD THEREFOR AND USE THEREOF

(71) Applicant: COCRYSTAL TECHNOLOGY (JIAXING) CO., LTD, Jiaxing (CN)

(72) Inventors: Xuefeng Mei, Shanghai (CN); Qi Zhang, Shanghai (CN); Junjie Bao, Shanghai (CN); Liye Lu, Shanghai (CN)

(73) Assignee: COCRYSTAL TECHNOLOGY (JIAXING) CO., LTD., Zhejiang (CN)

( * ) Notice: Subject to any disclaimer, the term of this patent is extended or adjusted under 35 U.S.C. 154(b) by 391 days.

(21) Appl. No.: 18/281,091

(22) PCT Filed: Mar. 7, 2022

(86) PCT No.: PCT/CN2022/079488

§ 371 (c)(1),
(2) Date: Sep. 8, 2023

(87) PCT Pub. No.: WO2022/188732

PCT Pub. Date: Sep. 15, 2022

(65) Prior Publication Data

US 2024/0140897 A1 May 2, 2024

(30) Foreign Application Priority Data

Mar. 10, 2021 (CN) ......................... 202110260473.5

(51) Int. Cl.

*C07C 50/28* (2006.01)
*C07C 46/10* (2006.01)
*C07D 213/82* (2006.01)

(52) U.S. Cl.

CPC .............. *C07C 50/28* (2013.01); *C07C 46/10* (2013.01); *C07D 213/82* (2013.01); *C07B 2200/13* (2013.01)

(58) Field of Classification Search

CPC ............................ C07C 50/28; C07B 2200/13
See application file for complete search history.

(56) References Cited

U.S. PATENT DOCUMENTS

2004/0197418 A1 10/2004 Ueda et al.

FOREIGN PATENT DOCUMENTS

| | | | |
|---|---|---|---|
| CN | 103635452 | A | 3/2014 |
| CN | 107721902 | A | 2/2018 |
| CN | 113024362 | A | 6/2021 |
| EP | 2025662 | A1 | 2/2009 |
| WO | 2008007415 | A1 | 1/2008 |
| WO | 2019/162429 | A1 | 8/2019 |

OTHER PUBLICATIONS

Brittain, "Polymorphism in Pharmaceutical Solids", 2009, Informa Healthcare USA, 2nd Ed., p. 318-346 (Year: 2009).*
International Search Report issued by the China National Intellectual Property Office in connection with International Application No. PCT/CN2022/079488, dated Apr. 24, 2022.
Extended European Search Report issued by the European Patent Office on Dec. 13, 2024 in corresponding EP Patent Application No. 22766256.6.

* cited by examiner

*Primary Examiner* — Brenda L Coleman
*Assistant Examiner* — Madeline E Braun
(74) *Attorney, Agent, or Firm* — Carter, DeLuca & Farrell LLP

(57) ABSTRACT

The present invention relates to a co-crystal of coenzyme QH and nicotinamide, a preparation method therefor and the use thereof. Compared with the existing coenzyme QH, the co-crystal has a higher melting point and superior stability. The preparation method for the co-crystal of coenzyme QH is simple, easy to control and good in terms of reproducibility. The present invention greatly improves the use convenience of coenzyme QH, saves costs during storage, transportation and use, and broadens the application range of coenzyme QH.

7 Claims, 9 Drawing Sheets

CO-CRYSTAL OF COENZYME QH AND NICOTINAMIDE, PREPARATION METHOD THEREFOR AND USE THEREOF

CROSS REFERENCE TO RELATED APPLICATIONS

The present application is a national stage application of International Application No. PCT/CN2022/079488, filed Mar. 7, 2022, which claims the benefit of and priority to Chinese Patent Application No. 202110260473.5, filed Mar. 10, 2021, the entire contents of each of which are hereby incorporated by reference herein in their entirety.

TECHNICAL FIELD

The invention relates to the technical field of coenzyme Q10, in particular to a co-crystal of reduced coenzyme Q10 (coenzyme QH) and nicotinamide and a preparation method therefor. Compared with the existing coenzyme QH, the co-crystal has a higher melting point and superior stability. The preparation method of the coenzyme QH co-crystal is simple, easy to control and good in terms of reproducibility. In the present invention, the convenience of using the coenzyme QH is greatly improved, the cost during storage, transportation and use is saved, and the application range of the coenzyme QH is broadened.

BACKGROUND ART

Coenzyme Q10, as the only coenzyme Q substance in the human body, is a fat-soluble compound widely present in organisms. It is a coenzyme that is not tightly bound to proteins in the respiratory chain, and plays an important role in proton translocation and electron transfer in the human respiratory chain. As an activator of cell metabolism and cellular respiration, coenzyme Q10 is also an important antioxidant and non-specific immune enhancer, which can inhibit mitochondrial peroxidation, promote oxidative phosphorylation, and protect the integrity of biofilm structure. In addition, coenzyme Q10 has an enhanced effect on immune non-specificity, can enhance the production of antibody, and improve T cell function. Coenzyme Q10 is essentially a metabolic activator, which can activate cellular respiration, accelerate the production of adenosine triphosphate, and play a first-aid role in detoxification. It can also change the hypoxic state of cells and tissues, has better protective and improving effects on liver, brain, heart and nervous system, and enhances the non-specific immune response in the body. So far, coenzyme Q10 has been widely used in foods, health products, cosmetics and pharmaceutical industries, and is favored by scholars and consumers.

Coenzyme Q10 may be present in two forms: oxidized form and reduced form. Usually, in the human body, 40 to 90% of coenzyme Q10 is present in the reduced form. Reduced coenzyme Q10 is often called coenzyme QH. Compared with oxidized coenzyme Q10, coenzyme QH has better antioxidant properties and more efficient absorption. However, coenzyme QH is easily oxidized in air and has poor stability, which limits its further application and development. In order to improve the stability of coenzyme QH, various methods have been used, such as addition of an antioxidant, preparations of new crystal form and co-crystal, etc.

CN102381948A and CN101318889A disclose methods for stabilizing coenzyme QH by adding ascorbic acid or its derivatives, wherein coenzyme QH was ground with 10% by mass of ascorbic acid or its derivatives and placed in air at 25° C. for 4 days, and about 13% of coenzyme QH was oxidized.

A stable polymorph of coenzyme QH is prepared in CN103635452A, but it is still oxidized after stored in the air for a long time. It was found that after the crystal was placed in the air at 25° C. for 28 days, about 6% of the coenzyme QH was oxidized.

WO2019162429A discloses seven co-crystals of coenzyme QH, among which the co-crystals of coenzyme QH with 3,4-dihydroxybenzoic acid or 3,5-dihydroxybenzoic acid have good stability. However, these two ligands are not suitable for large-scale use in food, and the preparation method of the co-crystals is complicated, requiring stirring in a solvent for 3 days or more.

Therefore, there is a need to further develop a stable coenzyme QH product.

SUMMARY OF THE INVENTION

In order to improve the stability of coenzyme QH products, a large number of experiments were attempted to form co-crystals with various compounds and coenzyme QH. The results revealed that a stable co-crystal can be formed by adding edible nicotinamide (one form of vitamin B3) as a ligand, thereby changing the intermolecular interaction and spatial arrangement of the coenzyme QH molecule at the molecular level, enhancing the stability of the coenzyme QH molecule against oxygen, increasing its melting point, and thus improving its chemical stability and broadening its application fields, while other similar compounds such as: nicotinic acid (one form of vitamin B3), riboflavin (vitamin B2), calcium pantothenate (vitamin B5), folic acid (vitamin B9) and ascorbic acid (vitamin C), etc., cannot form a co-crystal with coenzyme QH to increase the melting point of coenzyme QH and further improving its stability. Thereby, the technical solution of using nicotinamide and coenzyme QH to prepare co-crystal is established to solve the above-mentioned technical problem, and thus the present invention is completed.

The coenzyme QH co-crystal with more excellent stability can further broaden the application range of coenzyme QH. Therefore, the co-crystal of coenzyme QH and nicotinamide of the present invention has strong practical application value.

The first object of the present invention is to provide a co-crystal of coenzyme QH and nicotinamide.

The second object of the present invention is to provide a method for preparing the co-crystal of coenzyme QH and nicotinamide.

The third object of the present invention is to provide a product comprising the co-crystal of coenzyme QH and nicotinamide, wherein the product is selected from the group consisting of a health product, a food, a cosmetic, a medicine, a pharmaceutical excipient and a feed.

The fourth object of the present invention is to provide a use of the co-crystal of co-enzyme QH and nicotinamide in the preparation of a product selected from the group consisting of a health product, a food, a cosmetic, a medicine, a pharmaceutical excipient and a feed.

In a first aspect, the present invention provides a co-crystal of coenzyme QH and nicotinamide, wherein the stoichiometric ratio of coenzyme QH to nicotinamide is 1:1.

The co-crystal of coenzyme QH and nicotinamide has an X-ray powder diffraction pattern having characteristic peaks at 2θ angles of 4.3°±0.2°, 5.7°±0.2°, 17.1°±0.2°, 17.9°±0.2°, 18.9°±0.2°, 19.8°±0.2°, 20.8°±0.2° and 23.1°±0.2°; in particular, further having characteristic peaks at 2θ angles of about 8.4°±0.2°, 9.9°±0.2°, 18.6°±0.2°, 19.1°±0.2°, 27.8°±0.2° and 30.3°±0.2°. In particular, the co-crystal of coenzyme QH and nicotinamide has an X-ray powder diffraction pattern substantially as shown in FIG. 1.

Particularly, the co-crystal of coenzyme QH and nicotinamide has a differential scanning calorimetry pattern having a characteristic endothermic peak at about 57±2° C. when the temperature is increased at a rate of 10° C./min, as determined by differential scanning calorimetry; preferably, the co-crystal has a differential scanning calorimetry pattern substantially as shown in FIG. 2.

Particularly, the co-crystal of coenzyme QH and nicotinamide has an infrared spectrum having characteristic peaks at about 3465 $cm^{-1}$, 3170 $cm^{-1}$ and 1697 $cm^{-1}$; particularly, further having characteristic peaks at 2964 $cm^{-1}$, 2945 $cm^{-1}$, 2907 $cm^{-1}$, 2847 $cm^{-1}$, 1664 $cm^{-1}$, 1607 $cm^{-1}$, 1445 $cm^{-1}$, 1422 $cm^{-1}$, 1384 $cm^{-1}$, 1280 $cm^{-1}$, 1261 $cm^{-1}$, 1197 $cm^{-1}$, 1164 $cm^{-1}$, 1149 $cm^{-1}$, 1109 $cm^{-1}$, 1009 $cm^{-1}$, 907 $cm^{-1}$, 877 $cm^{-1}$, 795 $cm^{-1}$, 751 $cm^{-1}$, 599 $cm^{-1}$ and 475 $cm^{-1}$; particularly, the co-crystal has an infrared spectrum substantially as shown in FIG. 3.

In a second aspect, the present invention provides a method for preparing the co-crystal of coenzyme QH and nicotinamide, wherein said method is one of the following methods:

Method 1:

coenzyme QH and nicotinamide are recrystallized in a solvent to obtain a precipitate, which is dried to obtain the co-crystal of coenzyme QH and nicotinamide;

Method 2:

coenzyme QH and nicotinamide are subjected to ball milling in a solvent for 10 minutes or more, and the obtained solid is dried to obtain the co-crystal of coenzyme QH and nicotinamide.

The solvent is selected from solvents that have certain solubility to the raw materials and do not cause deterioration of the raw materials. Preferably the solvent is one or more selected from the group consisting of water, an alcohol, a ketone, an ester, an alkane, an aromatic hydrocarbon and a halogenated alkane; more preferably, the solvent is one or more selected from the group consisting of methanol, ethanol, isopropanol, ethyl acetate, isopropyl acetate, acetone, methyl tert-butyl ether, n-hexane and n-heptane.

The preparation method of the present invention is simple to operate and easy to control the crystallization with high crystallinity and good reproducibility, and thus can stably obtain the co-crystal of coenzyme QH and nicotinamide.

In a third aspect, the present invention provides a coenzyme QH composition, comprising the co-crystal of coenzyme QH and nicotinamide.

In some embodiments, in addition to the co-crystal of coenzyme QH and nicotinamide of the present invention, the coenzyme QH composition may comprise an excess amount of nicotinamide, or an excess amount of coenzyme QH, and an other pharmaceutically acceptable excipient. That is to say, in the raw materials of the coenzyme QH composition, the molar ratio of coenzyme QH to nicotinamide is not particularly limited, as long as the co-crystal of coenzyme QH and nicotinamide can be prepared from the raw materials of the coenzyme QH composition. For example, the molar ratio of coenzyme QH to nicotinamide in the coenzyme QH composition may be 2:1 to 1:2, wherein parts of the components exist in the form of the co-crystal of coenzyme QH and nicotinamide, while the other parts of the components exist in free form. It is preferable that all of coenzyme QH forms the co-crystal to overcome the defects of low melting point and poor stability of coenzyme QH. The other excipient is not particularly limited, and can vary according to the purpose of application. For example, when applied to medicines, it may be a pharmaceutically acceptable excipient; when applied to health products, it may be an acceptable excipient in health products; when applied to food, it may be a food acceptable excipient; when applied to cosmetics, it may be a cosmetically acceptable excipient; and when applied to feed, it may be an acceptable excipient in feed.

In some embodiments, the stoichiometric ratio of coenzyme QH to nicotinamide in the coenzyme QH composition is 2:1. The coenzyme QH composition with a stoichiometric ratio of coenzyme QH to nicotinamide of 2:1 has an X-ray powder diffraction pattern having characteristic peaks at 2θ angles of about 4.3°±0.2°, 5.7°±0.2°, 8.4°±0.2°, 9.9°±0.2°, 17.1°±0.2°, 17.9°±0.2°, 18.6°±0.2°, 18.9°±0.2°, 19.1°±0.2°, 19.8°±0.2°, 20.8°±0.2°, 27.8°±0.2° and 30.3°±0.2°.

The coenzyme QH composition with a stoichiometric ratio of coenzyme QH to nicotinamide of 2:1 has an X-ray powder diffraction pattern substantially as shown in FIG. 4.

The coenzyme QH composition with a stoichiometric ratio of coenzyme QH to nicotinamide of 2:1 has a differential scanning calorimetry pattern having a characteristic endothermic peak at about 57±2° C. when the temperature is increased at a rate of 10° C./min, as determined by differential scanning calorimetry; preferably, the coenzyme QH composition has a differential scanning calorimetry pattern substantially as shown in FIG. 5.

The coenzyme QH composition with a stoichiometric ratio of coenzyme QH to nicotinamide of 2:1 has an infrared spectrum having characteristic peaks at about 3465 $cm^{-1}$, 3195 $cm^{-1}$, 2964 $cm^{-1}$, 2945 $cm^{-1}$, 2909 $cm^{-1}$, 2848 $cm^{-1}$, 1696 $cm^{-1}$, 1664 $cm^{-1}$, 1607 $cm^{-1}$, 1445 $cm^{-1}$, 1427 $cm^{-1}$, 1384 $cm^{-1}$, 1280 $cm^{-1}$, 1261 $cm^{-1}$, 1197 $cm^{-1}$, 1164 $cm^{-1}$, 1149 $cm^{-1}$, 1109 $cm^{-1}$, 1009 $cm^{-1}$, 907 $cm^{-1}$, 877 $cm^{-1}$, 795 $cm^{-1}$, 751 $cm^{-1}$, 599 $cm^{-1}$ and 475 $cm^{-1}$; preferably, the coenzyme QH composition has an infrared spectrum substantially as shown in FIG. 6.

In still other embodiments, the stoichiometric ratio of coenzyme QH to nicotinamide in the coenzyme QH composition is 1:1.5.

The coenzyme QH composition with a stoichiometric ratio of coenzyme QH to nicotinamide of 1:1.5 has an X-ray powder diffraction pattern having characteristic peaks at 2θ angles of about 4.3°±0.2°, 5.7°±0.2°, 8.4°±0.2°, 9.9°±0.2°, 17.1°±0.2°, 17.9°±0.2°, 18.6°±0.2°, 18.9°±0.2°, 19.1°±0.2°, 19.8°±0.2°, 20.8°±0.2°, 27.8°±0.2° and 30.3°±0.2°.

The coenzyme QH composition with a stoichiometric ratio of coenzyme QH to nicotinamide of 1:1.5 has an X-ray powder diffraction pattern substantially as shown in FIG. 7.

The coenzyme QH composition with a stoichiometric ratio of coenzyme QH to nicotinamide of 1:1.5 has a differential scanning calorimetry pattern having a characteristic endothermic peak at about 57±2° C. when the temperature is increased at a rate of 10° C./min, as determined by differential scanning calorimetry; preferably, the coenzyme QH composition has a differential scanning calorimetry pattern substantially as shown in FIG. 8.

The coenzyme QH composition with a stoichiometric ratio of coenzyme QH to nicotinamide of 1:1.5 has an infrared spectrum having characteristic peaks at about 3465 $cm^{-1}$, 3367 $cm^{-1}$, 3167 $cm^{-1}$, 2944 $cm^{-1}$, 2909 $cm^{-1}$, 2845 $cm^{-1}$, 1697 $cm^{-1}$, 1681 $cm^{-1}$, 1619 $cm^{-1}$, 1445 $cm^{-1}$, 1422 $cm^{-1}$, 1384 $cm^{-1}$, 1280 $cm^{-1}$, 1261 $cm^{-1}$, 1197 $cm^{-1}$, 1164 $cm^{-1}$, 1149 $cm^{-1}$, 1109 $cm^{-1}$, 1009 $cm^{-1}$, 907 $cm^{-1}$, 877 $cm^{-1}$, 795 $cm^{-1}$, 751 $cm^{-1}$, 599 $cm^{-1}$ and 475 $cm^{-1}$; preferably, the coenzyme QH composition has an infrared spectrum substantially as shown in FIG. 9.

In still other embodiments, the stoichiometric ratio of coenzyme QH to nicotinamide in the coenzyme QH composition is 1:2.

The coenzyme QH composition with a stoichiometric ratio of coenzyme QH to nicotinamide of 1:2 has an X-ray powder diffraction pattern having characteristic peaks at 2θ angles of about 4.3°±0.2°, 5.7°±0.2°, 8.4°±0.2°, 9.9°±0.2°, 14.8°±0.2°, 17.1°±0.2°, 17.9°±0.2°, 18.6°±0.2°, 18.9°±0.2°, 19.1°±0.2°, 19.8°±0.2°, 20.8°±0.2°, 25.3°±0.2°, 25.8°±0.2°, 27.3°±0.2°, 27.8°±0.2° and 30.3°±0.2°.

The coenzyme QH composition with a stoichiometric ratio of coenzyme QH to nicotinamide of 1:2 has an X-ray powder diffraction pattern substantially as shown in FIG. 10.

The coenzyme QH composition with a stoichiometric ratio of coenzyme QH to nicotinamide of 1:2 has a differential scanning calorimetry pattern having a characteristic endothermic peak at about 57±2° C. when the temperature is increased at a rate of 10° C./min, as determined by differential scanning calorimetry; preferably, the coenzyme QH composition has a differential scanning calorimetry pattern substantially as shown in FIG. 11.

The coenzyme QH composition with a stoichiometric ratio of coenzyme QH to nicotinamide of 1:2 has an infrared spectrum having characteristic peaks at about 3465 $cm^{-1}$, 3367 $cm^{-1}$, 3167 $cm^{-1}$, 2944 $cm^{-1}$, 2909 $cm^{-1}$, 2845 $cm^{-1}$, 1697 $cm^{-1}$, 1681 $cm^{-1}$, 1619 $cm^{-1}$, 1445 $cm^{-1}$, 1422 $cm^{-1}$, 1384 $cm^{-1}$, 1280 $cm^{-1}$, 1261 $cm^{-1}$, 1197 $cm^{-1}$, 1164 $cm^{-1}$, 1149 $cm^{-1}$, 1109 $cm^{-1}$, 1009 $cm^{-1}$, 907 $cm^{-1}$, 877 $cm^{-1}$, 795 $cm^{-1}$, 751 $cm^{-1}$, 599 $cm^{-1}$ and 475 $cm^{-1}$; preferably, the coenzyme QH composition has an infrared spectrum substantially as shown in FIG. 12.

In another aspect, the present invention provides a coenzyme QH product comprising the co-crystal of the coenzyme QH and nicotinamide or the coenzyme QH composition, wherein the product is selected from the group consisting of a health product, a food, a cosmetic, a medicine, a pharmaceutical excipient and a feed.

In yet another aspect, the present invention provides a use of the co-crystal of coenzyme QH and nicotinamide or the coenzyme QH composition in the preparation of a coenzyme QH product, wherein the product is selected from the group consisting of a health product, a food, a cosmetic, a medicine, a pharmaceutical excipient and a feed.

Other suitable raw materials required by the product can also be included in the product, for example, the food may comprise a food main ingredient and an edible food additive acceptable in food, such as a sweetener, a flavoring agent, a preservative, a fragrance, a colorant, etc.; the cosmetic may comprise a cosmetically acceptable cosmetic main ingredient and an additive, such as a solvent, a fragrance, a preservative, a flavor, a colorant etc.; the medicine may comprise a pharmaceutically active ingredient and a pharmaceutically acceptable excipient, such as a carrier, a diluent, an adjuvant, a colorant etc.; the feed can comprise a feed main ingredient, such as soybean meal, hay etc., and an acceptable feed auxiliary material in feed, such as a sweetener, a flavoring agent, a preservative, a fragrance, a colorant etc., but the present invention is not limited thereto.

The above product is prepared by adding the co-crystal of coenzyme QH and nicotinamide according to the present invention or the coenzyme QH composition according to the present invention. Except for adding the co-crystal of coenzyme QH and nicotinamide of the present invention or the coenzyme QH composition of the present invention, the preparation method of the product can be prepared according to a conventional method.

In the present invention, the X-ray powder diffraction pattern is recorded on a Bruker D8 Advanced X-ray diffractometer, with a Cu-Kα irradiation (λ=1.54056 Å), a scanning range of a 2θ interval from 3° to 40°, and a scanning rate of 5°/min.

The differential scanning calorimetry was performed on a TA DSC Q2000 equipment with a heating rate of 10 K/min.

Thermo Scientific Nicolet 6700 was used as a Fourier transform infrared spectrometer.

Ball milling was performed in a Jingxin JX-2G planetary ball mill.

Agilent 1260 Infinity HPLC was used for liquid chromatography.

The present invention has been described in detail above, but the above-described embodiments are merely illustrative in nature and are not intended to limit the present invention. Furthermore, the present invention is not to be bound by any theory presented in the preceding prior art or summary of the invention, or the following examples.

Unless expressly stated otherwise, throughout this specification, numerical ranges include any sub-range therein and any numerical value in the increments by the smallest subunit of a given value therein. Unless expressly stated otherwise, throughout this specification numerical values represent approximate measures or limitations of ranges that include minor deviations from the given values and embodiments having about the stated value as well as having the exact value stated. Except in the working examples provided at the end of the detailed description, all numerical values of parameters (e.g., amounts or conditions) in this specification (including the appended claims) should in all cases be understood to be understood by the term "about" modifier, regardless of whether "about" actually precedes the numerical value. "About" indicates that the stated value allows for some imprecision (some close to exactness in the value; about or reasonably close to the value; approximation). If the imprecision provided by "about" is not understood in the art with this ordinary meaning, then "about" as used herein at least indicates the variation that can be produced by ordinary methods of measuring and using these parameters. For example, "about" may include variations of 10% or less, 5% or less, 4% or less, 3% or less, 2% or less, 1% or less, or 0.5% or less, and in some respects, a variation of 0.1% or less.

Unless expressly stated otherwise, the terms "comprising", "including", "having", "containing" or any other similar terms throughout the application documents are open-ended terms, which means that a co-crystal or article may comprises, in addition to the elements listed herein, other elements which are not specifically listed herein but are generally inherent in a co-crystal or article. In addition, the interpretation of the terms "comprising", "including", "having" and "containing" used herein should be deemed to specifically disclose and also cover closed or semi-closed conjunctions such as "consisting of" and "consisting essentially of". "Consisting essentially of" means that the elements listed herein comprises 95% or more, 97% or more, or in some aspects, 99% or more of the co-crystal or article.

Beneficial Effect

The invention provides a stable co-crystal of coenzyme QH and nicotinamide. Compared with the coenzyme QH itself, the co-crystal has significantly improved chemical stability. The method for preparing the co-crystal of coenzyme QH of the invention is simple with good reproducibility, and has the advantages of low cost, environmental friendliness and easy control. In addition, the co-crystal of the invention has more excellent chemical stability, and thus can further broaden the application range of coenzyme QH. Therefore, the co-crystal of coenzyme QH and nicotinamide has strong practical application value.

MODE OF THE INVENTION

In order to make the objects, technical solutions and advantages of the present invention more clear, the present invention will be further described in detail below in conjunction with the accompanying drawings and examples. It should be understood that the specific examples described here are only used to explain the present invention, not to limit the present invention.

Example 1

To 100 g of 95% ethanol, 10 g of oxidized coenzyme Q10 and 6 g of L-ascorbic acid were added. The mixture was stirred at 78° C. for reduction for 20 hours, cooled to 0° C. and kept stirring at this temperature for 1 hour. The mixture was filtered under reduced pressure. The filter cake was washed three times with 95% ethanol, and dried under reduced pressure to obtain a white powder. All operations were performed under nitrogen protection except for drying under reduced pressure. The weight ratio of coenzyme QH/oxidized coenzyme Q10 in the obtained sample was 99.2/0.8.

Figure 13:
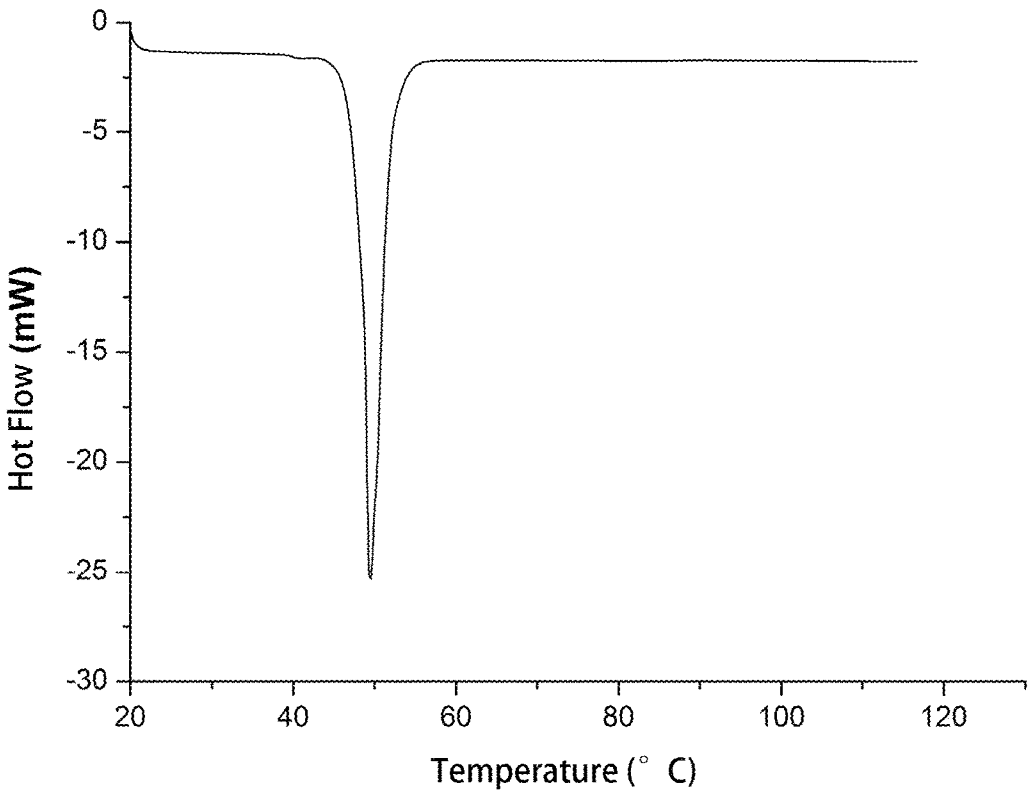
FIG. 13 is a differential scanning calorimetry (DSC) pattern of the coenzyme QH itself prepared in Example 1 of the present invention.

The powder was detected by differential scanning calorimetry (DSC), and the result is shown in FIG. 13. It can be seen from FIG. 13 that QH had a characteristic endothermic peak at about 49° C.

Example 2

0.4 g of nicotinamide and 1 g of the coenzyme QH obtained in Example 1 were added to 10 ml of a solvent of isopropanol/isopropyl acetate=1/1, stirred at 40° C. to be dissolved, and recrystallized to obtain a white precipitate, which was filtered through a Buchner funnel. The solid was dried in a vacuum oven at room temperature for 12 hours to obtain a co-crystal of coenzyme QH and nicotinamide.

The contents of coenzyme QH and nicotinamide in the co-crystal of coenzyme QH and nicotinamide obtained were measured respectively by high performance liquid chromatography, and it was found that the content of coenzyme QH was about 86.1%, and the content of nicotinamide was about 12.6%, indicating that in this co-crystal, the stoichiometric ratio of coenzyme QH to nicotinamide was about 1:1.

This co-crystal was characterized by solid state methods such as X-ray powder diffraction (XRPD), differential scanning calorimetry (DSC) and infrared (IR) spectroscopy. The results are shown in FIGS. 1-3 respectively.

Figure 1:
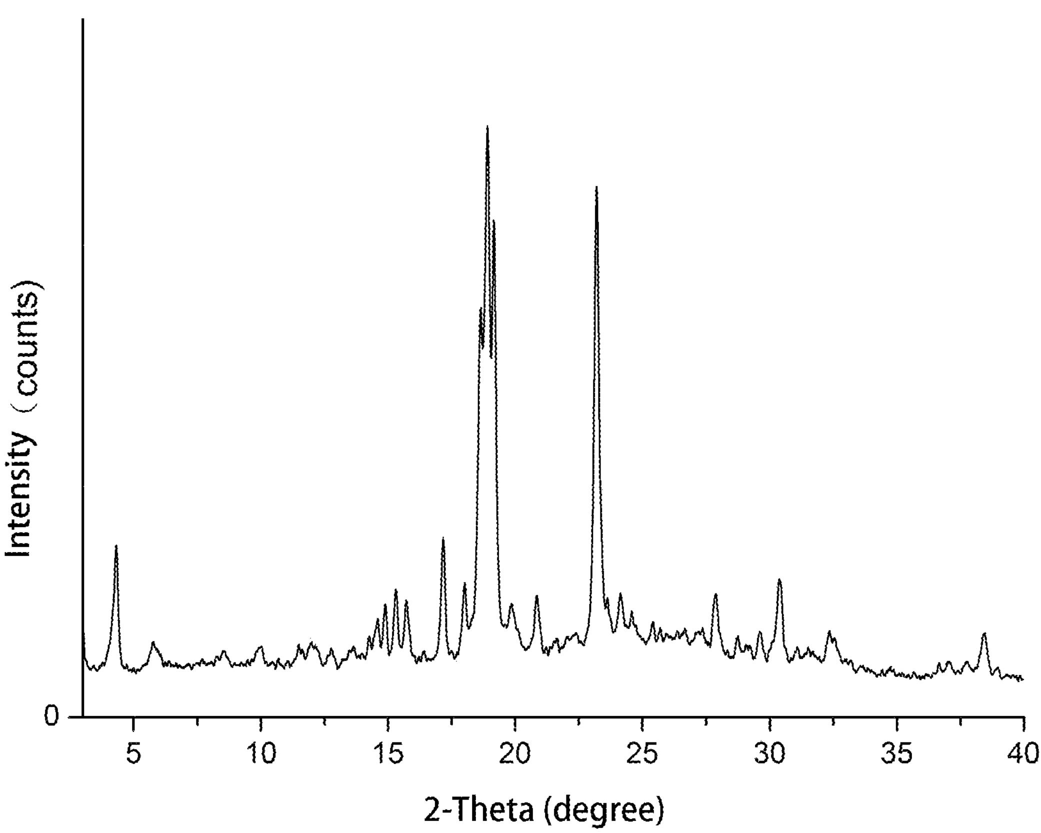
FIG. 1 is an X-ray powder diffraction (XRPD) pattern of the co-crystal comprising coenzyme QH and nicotinamide with a stoichiometric ratio of 1:1 provided by the present invention.

As shown in FIG. 1, the co-crystal of coenzyme QH and nicotinamide had an X-ray powder diffraction pattern having characteristic peaks at 2θ angles of about 4.3°, 5.7°, 8.4°, 9.9°, 17.1°, 17.9°, 18.6, 18.9°, 19.1°, 19.8°, 20.8°, 23.1°, 27.8°, 30.3°, etc.

Figure 2:
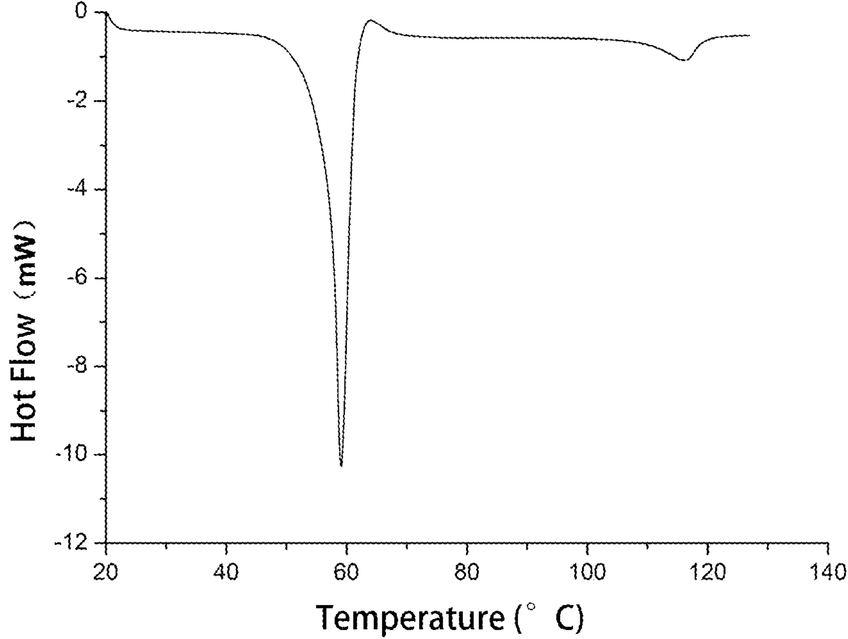
FIG. 2 is a differential scanning calorimetry (DSC) pattern of the co-crystal comprising coenzyme QH and nicotinamide with a stoichiometric ratio of 1:1 provided by the present invention.

As shown in FIG. 2, the co-crystal of coenzyme QH and nicotinamide had a differential scanning calorimetry pattern having a characteristic endothermic peak at about 57° C.

Figure 3:
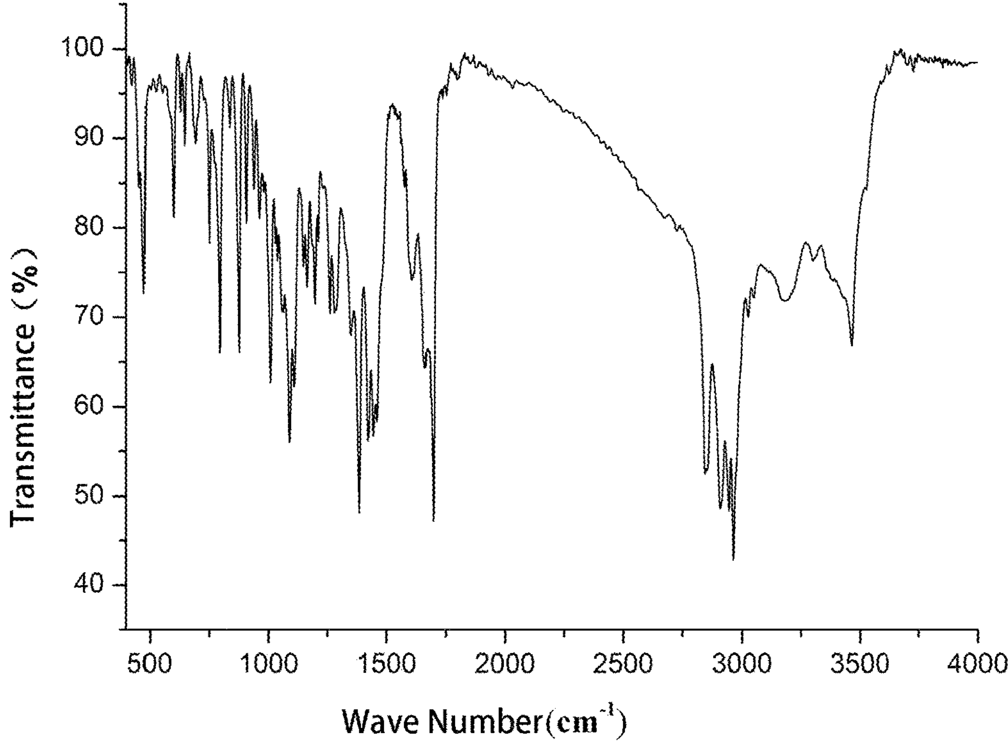
FIG. 3 is an infrared (IR) spectrum of the co-crystal comprising coenzyme QH and nicotinamide with a stoichiometric ratio of 1:1 provided by the present invention.

As shown in FIG. 3, the co-crystal of coenzyme QH and nicotinamide had an infrared spectrum having characteristic peaks at about 3465 $cm^{-1}$, 3170 $cm^{-1}$, 2964 $cm^{-1}$, 2945 $cm^{-1}$, 2907 $cm^{-1}$, 2847 $cm^{-1}$, 1697 $cm^{-1}$, 1664 $cm^{-1}$, 1607

$cm^{-1}$, 1445 $cm^{-1}$, 1422 $cm^{-1}$, 1384 $cm^{-1}$, 1280 $cm^{-1}$, 1261 $cm^{-1}$, 1197 $cm^{-1}$, 1164 $cm^{-1}$, 1149 $cm^{-1}$, 1109 $cm^{-1}$, 1009 $cm^{-1}$, 907 $cm^{-1}$, 877 $cm^{-1}$, 795 $cm^{-1}$, 751 $cm^{-1}$, 599 $cm^{-1}$ and 475 $cm^{-1}$.

Example 3

0.122 g of nicotinamide and 0.87 g of the coenzyme QH obtained in Example 1 were added to 2 ml of ethanol, stirred at 60° C. to be dissolved, and recrystallized to obtain a white solid. The solid was dried in a vacuum oven at room temperature for 12 hours to obtain a co-crystal of coenzyme QH and nicotinamide.

The contents of coenzyme QH and nicotinamide in the co-crystal of coenzyme QH and nicotinamide obtained were measured respectively by high performance liquid chromatography, and it was found that the content of coenzyme QH was about 84.0%, and the content of nicotinamide was about 11.8%, indicating that in this co-crystal, the stoichiometric ratio of coenzyme QH to nicotinamide was about 1:1.

This co-crystal was characterized by solid state methods such as X-ray powder diffraction (XRPD), differential scanning calorimetry (DSC) and infrared (IR) spectroscopy. The results were basically consistent with the detection results of the co-crystal of coenzyme QH and nicotinamide in Example 2 respectively.

Example 4

0.244 g of nicotinamide and 1.72 g of the coenzyme QH obtained in Example 1 were added to a ball mill jar, and 1 ml of ethanol was added thereto. The ball milling was performed for 2 hours. The solid was dried in a vacuum oven at room temperature for 12 hours to obtain a co-crystal of coenzyme QH and nicotinamide.

This co-crystal was characterized by solid state methods such as X-ray powder diffraction (XRPD), differential scanning calorimetry (DSC) and infrared (IR) spectroscopy. The results were basically consistent with the detection results of the co-crystal of coenzyme QH and nicotinamide in Example 2 respectively.

Example 5

0.244 g of nicotinamide and 1.72 g of the coenzyme QH obtained in Example 1 were added to a ball mill jar, and 1 ml of a solvent of isopropanol/isopropyl acetate=1/1 was added thereto. The ball milling was performed for 2 hours. The solid was dried in a vacuum oven at room temperature for 12 hours to obtain a co-crystal of coenzyme QH and nicotinamide.

This co-crystal was characterized by solid state methods such as X-ray powder diffraction (XRPD), differential scanning calorimetry (DSC) and infrared (IR) spectroscopy. The results were basically consistent with the detection results of the co-crystal of coenzyme QH and nicotinamide in Example 2 respectively.

Example 6

0.122 g of nicotinamide and 1.72 g of the coenzyme QH obtained in Example 1 were added to a ball mill jar, and 1 ml of ethanol was added thereto. The ball milling was performed for 2 hours. The solid was dried in a vacuum oven at room temperature for 12 hours to obtain a coenzyme QH composition, wherein the stoichiometric ratio of coenzyme QH to nicotinamide is 2:1.

This coenzyme QH composition was characterized by solid state methods such as X-ray powder diffraction (XRPD), differential scanning calorimetry (DSC) and infrared (IR) spectroscopy. The results are shown in FIGS. 4-6 respectively.

Figure 4:
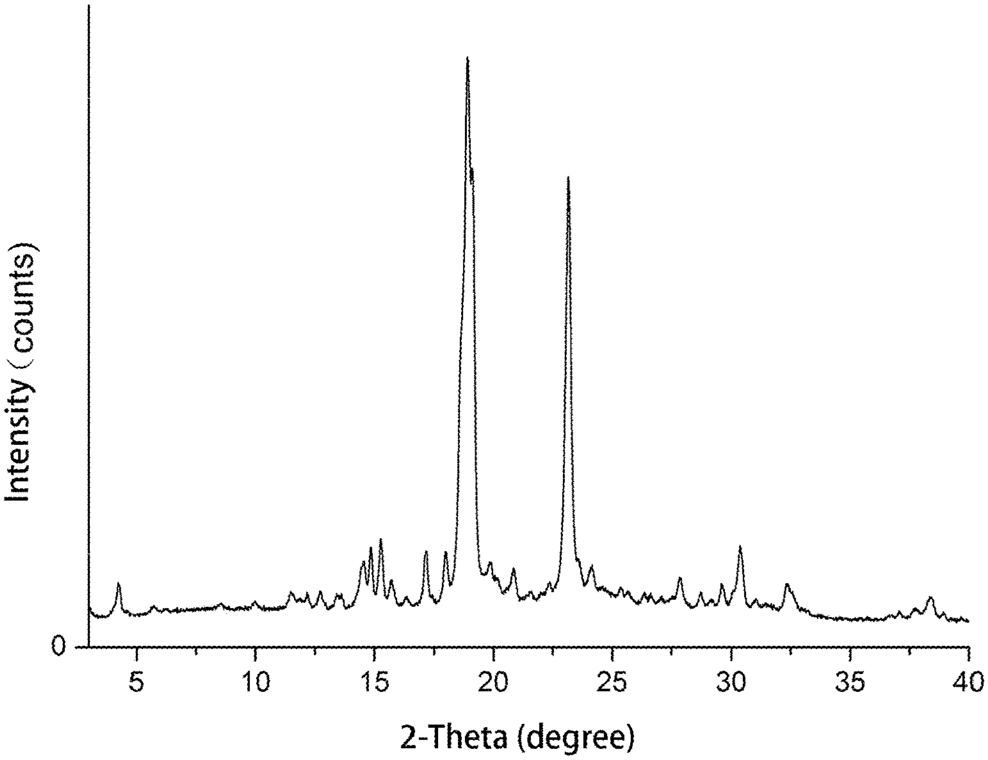
FIG. 4 is an X-ray powder diffraction (XRPD) pattern of the composition comprising coenzyme QH and nicotinamide with a stoichiometric ratio of 2:1 provided by the present invention.

It can be seen from the X-ray powder diffraction (XRPD) pattern in FIG. 4 that the coenzyme QH composition had an X-ray powder diffraction pattern having the characteristic peaks of the co-crystal of coenzyme QH and nicotinamide at 2θ angles of about 4.3°, 5.7°, 17.1°, 17.9°, 18.9°, 19.8°, 20.8° and 23.1°, indicating that the coenzyme QH composition comprises the co-crystal of coenzyme QH and nicotinamide.

Figure 5:
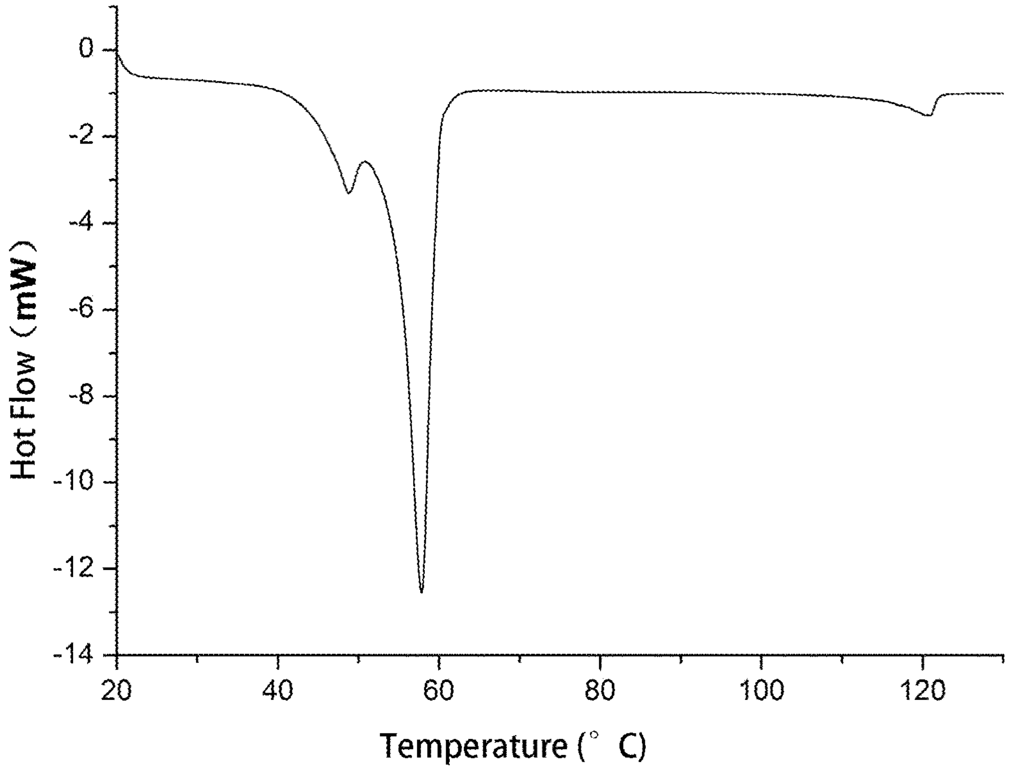
FIG. 5 is a differential scanning calorimetry (DSC) pattern of the composition comprising coenzyme QH and nicotinamide with a stoichiometric ratio of 2:1 provided by the present invention.

It can be seen from the differential scanning calorimetry (DSC) pattern in FIG. 5 that the coenzyme QH composition had a differential scanning calorimetry pattern having a characteristic endothermic peaks at about 50° C.-60° C., wherein the former peak was basically consistent with the melting peak of coenzyme QH, and the latter peak was generally consistent with that of the co-crystal, indicating that the composition was composed of coenzyme QH and the co-crystal of coenzyme QH and nicotinamide.

Figure 6:
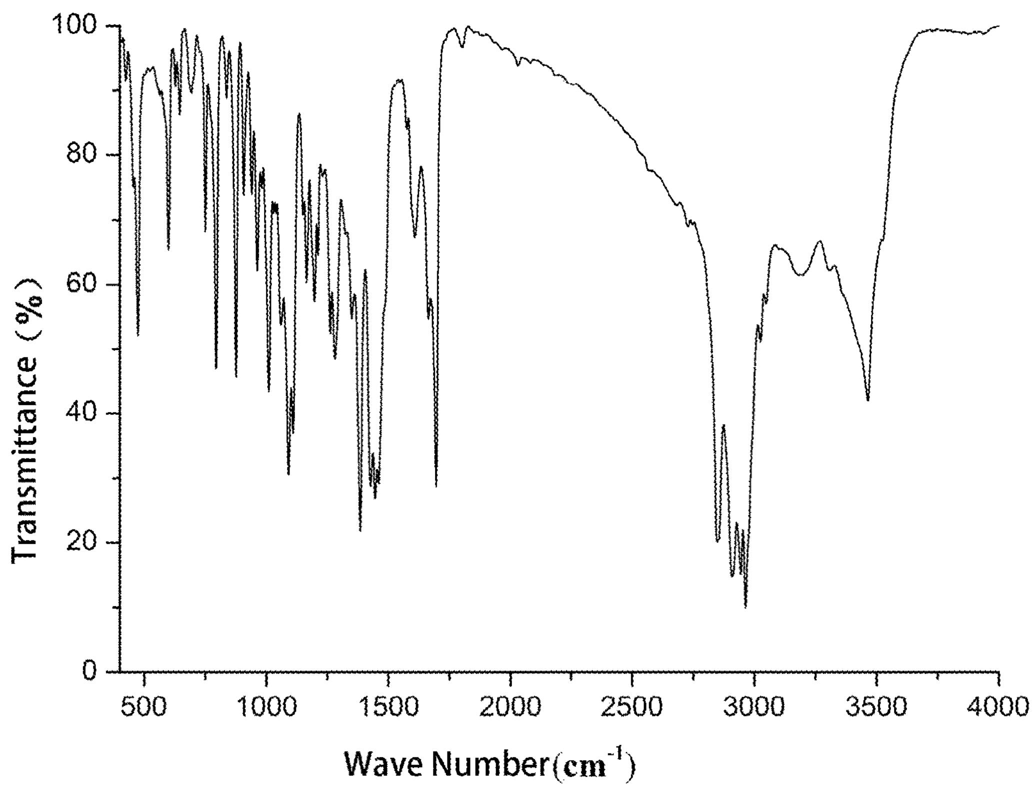
FIG. 6 is an infrared (IR) spectrum of the composition comprising coenzyme QH and nicotinamide with a stoichiometric ratio of 2:1 provided by the present invention.

It can be seen from the infrared spectrum in FIG. 6 that the coenzyme QH composition had an infrared spectrum having the characteristic peaks of the co-crystal of coenzyme QH and nicotinamide at 3465 $cm^{-1}$, 3170 $cm^{-1}$ and 1697 $cm^{-1}$, indicating that the coenzyme QH composition comprises the co-crystal of the coenzyme QH and nicotinamide.

Example 7

0.366 g of nicotinamide and 1.72 g of the coenzyme QH obtained in Example 1 were added to a ball mill jar, and 1 ml of ethanol was added thereto. The ball milling was performed for 2 hours. The solid was dried in a vacuum oven at room temperature for 12 hours to obtain a coenzyme QH composition, wherein the stoichiometric ratio of coenzyme QH to nicotinamide was 1:1.5.

This coenzyme QH composition was characterized by solid state methods such as X-ray powder diffraction (XRPD), differential scanning calorimetry (DSC) and infrared (IR) spectroscopy. The results are shown in FIGS. 7-9 respectively.

Figure 7:
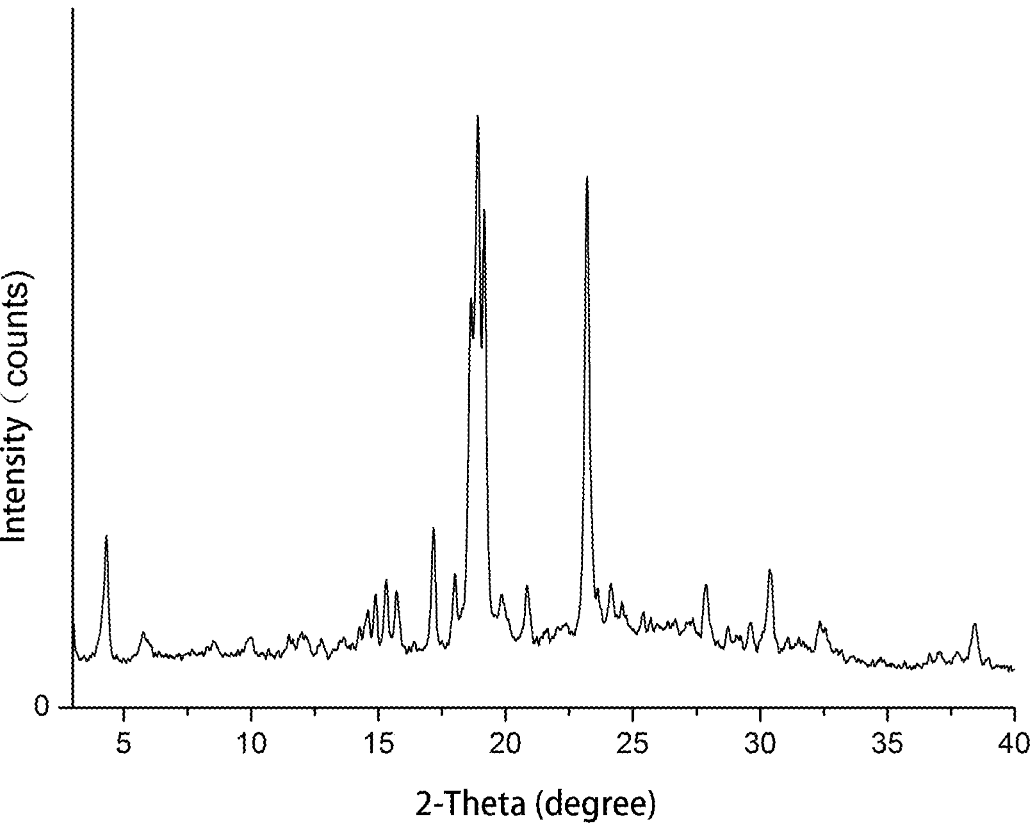
FIG. 7 is an X-ray powder diffraction (XRPD) pattern of the composition comprising coenzyme QH and nicotinamide with a stoichiometric ratio of 1:1.5 provided by the present invention.

It can be seen from the X-ray powder diffraction (XRPD) pattern in FIG. 7 that the coenzyme QH composition had an X-ray powder diffraction pattern having the characteristic peaks of the co-crystal of coenzyme QH and nicotinamide at 2θ angles of about 4.3°, 5.7°, 17.1°, 17.9°, 18.9°, 19.8°, 20.8° and 23.1°, indicating that the coenzyme QH composition comprises the co-crystal of coenzyme QH and nicotinamide.

Figure 8:
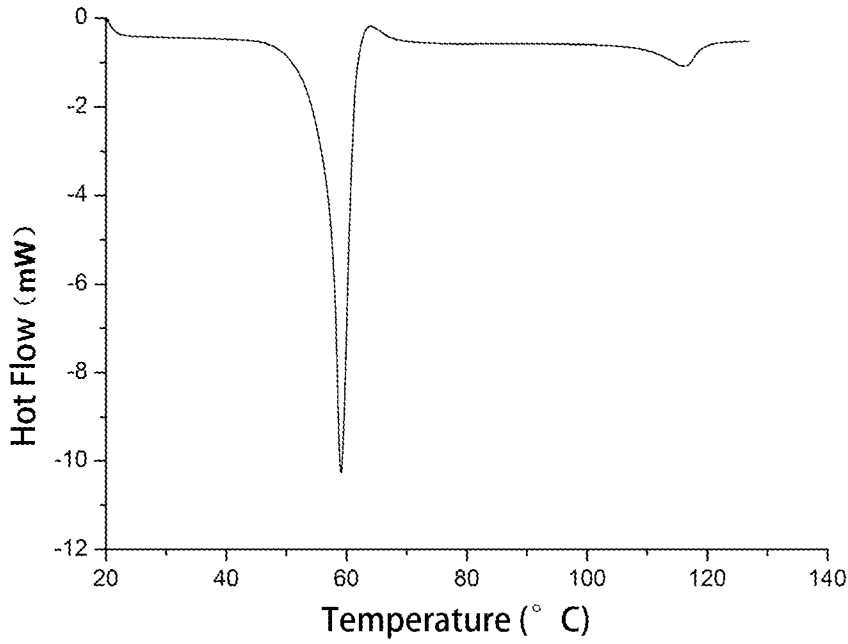
FIG. 8 is a differential scanning calorimetry (DSC) pattern of the composition comprising coenzyme QH and nicotinamide with a stoichiometric ratio of 1:1.5 provided by the present invention.

It can be seen from the differential scanning calorimetry (DSC) pattern in FIG. 8 that the coenzyme QH composition had a differential scanning calorimetry pattern having a characteristic endothermic peak at about 56° C., which was generally consistent with that of the co-crystal of coenzyme QH and nicotinamide.

Figure 9:
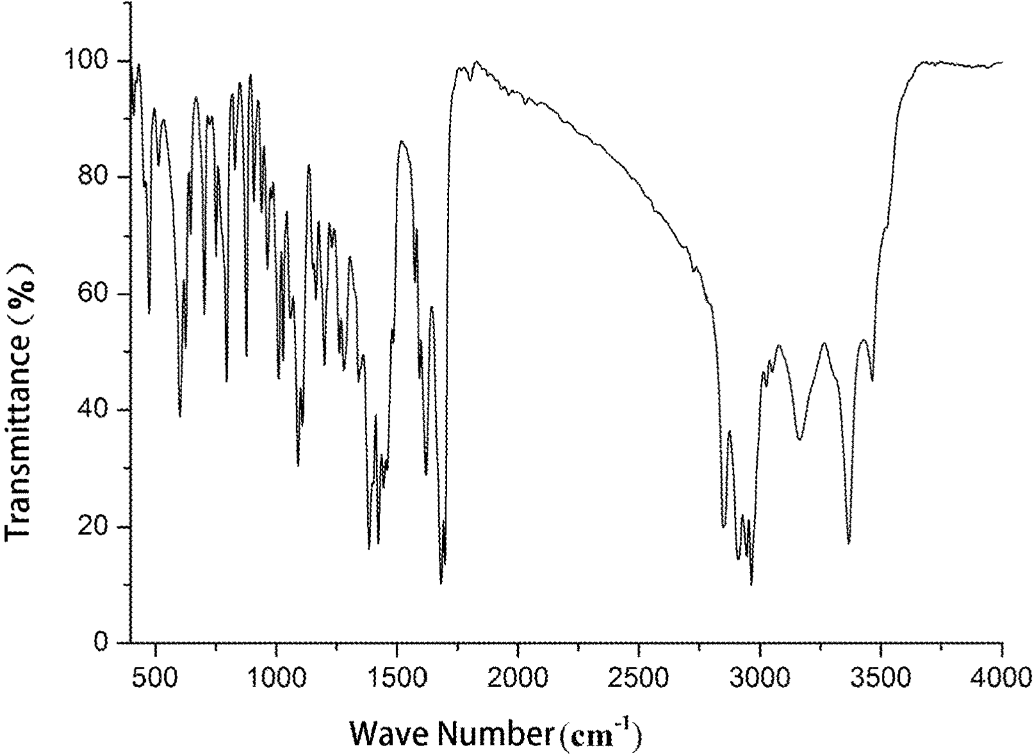
FIG. 9 is an infrared (IR) spectrum of the composition comprising coenzyme QH and nicotinamide with a stoichiometric ratio of 1:1.5 provided by the present invention.

It can be seen from the infrared spectrum in FIG. 9 that the coenzyme QH composition had an infrared spectrum having the characteristic peaks of the co-crystal of coenzyme QH and nicotinamide at 3465 $cm^{-1}$, 3170 $cm^{-1}$ and 1697 $cm^{-1}$, indicating that the coenzyme QH composition comprises the co-crystal of coenzyme QH and nicotinamide. At the same time, there was a characteristic peak of nicotinamide at 3368 cm$^{-1}$, indicating that the composition is composed of nicotinamide and the co-crystal of coenzyme QH and nicotinamide.

Example 8

0.488 g of nicotinamide and 1.72 g of the coenzyme QH obtained in Example 1 were added to a ball mill jar, and 1 ml of ethanol was added thereto. The ball milling was performed for 2 hours. The solid was dried in a vacuum oven at room temperature for 12 hours to obtain a coenzyme QH composition, wherein the stoichiometric ratio of coenzyme QH to nicotinamide was 1:2.

This coenzyme QH composition was characterized by solid state methods such as X-ray powder diffraction (XRPD), differential scanning calorimetry (DSC) and infrared (IR) spectroscopy. The results are shown in FIGS. 10-12 respectively.

Figure 10:
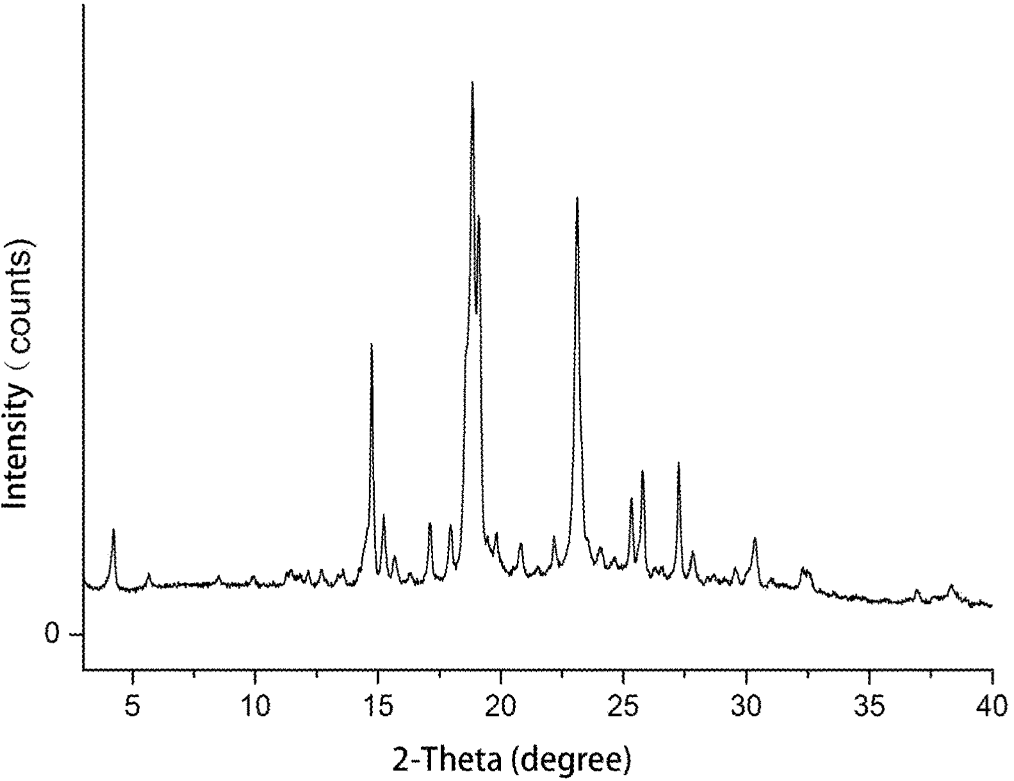
FIG. 10 is an X-ray powder diffraction (XRPD) pattern of the composition comprising coenzyme QH and nicotinamide with a stoichiometric ratio of 1:2 provided by the present invention.

It can be seen from the X-ray powder diffraction (XRPD) pattern in FIG. 10 that the coenzyme QH composition had an X-ray powder diffraction pattern having the characteristic peaks of the co-crystal of coenzyme QH and nicotinamide at 2θ angles of about 4.3°, 5.7°, 17.1°, 17.9°, 18.9°, 19.8°, 20.8° and 23.1°, indicating that the coenzyme QH composition comprises the co-crystal of coenzyme QH and nicotinamide.

Figure 11:
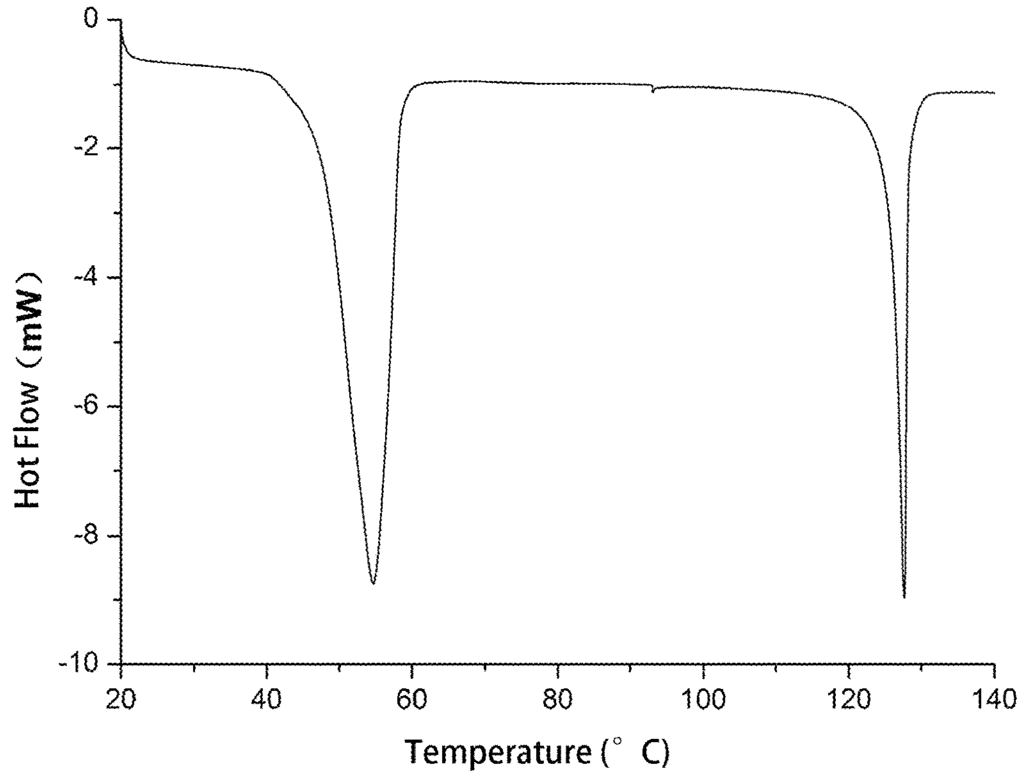
FIG. 11 is a differential scanning calorimetry (DSC) pattern of the composition comprising coenzyme QH and nicotinamide with a stoichiometric ratio of 1:2 provided by the present invention.

It can be seen from the differential scanning calorimetry (DSC) pattern in FIG. 11 that the coenzyme QH composition had a differential scanning calorimetry pattern having a characteristic endothermic peak at about 56° C., which was generally consistent with that of the co-crystal of coenzyme QH and nicotinamide.

Figure 12:
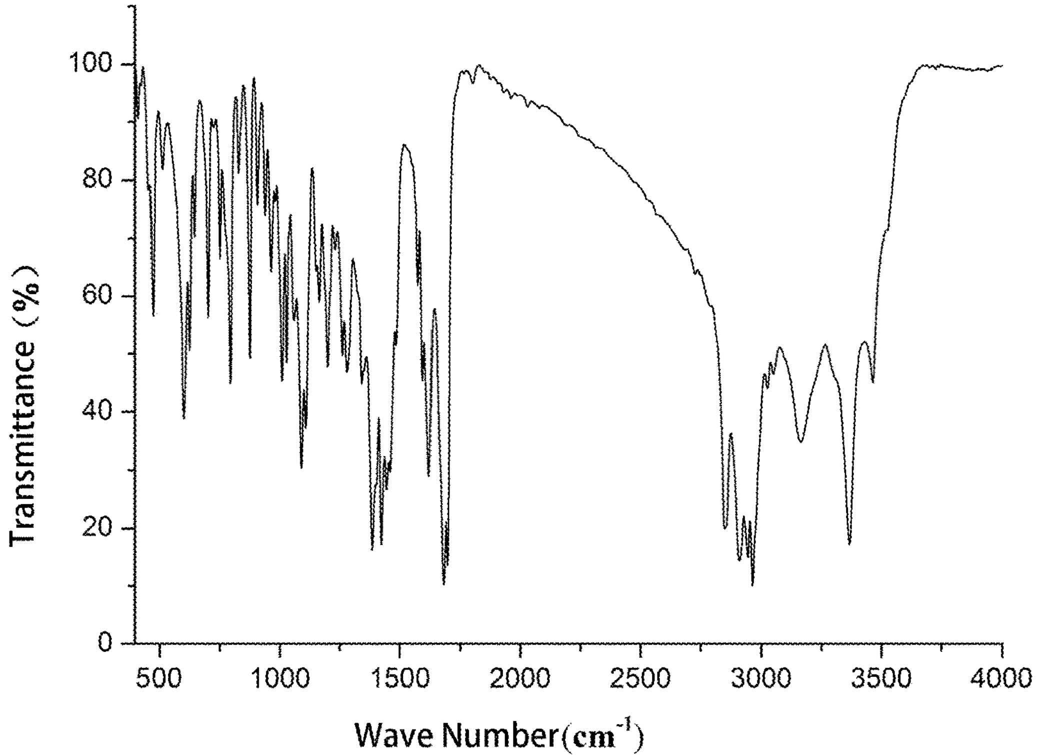
FIG. 12 is an infrared (IR) spectrum of the composition comprising coenzyme QH and nicotinamide with a stoichiometric ratio of 1:2 provided by the present invention.

It can be seen from the infrared spectrum in FIG. 12 that the coenzyme QH composition had an infrared spectrum having the characteristic peaks of the co-crystal of coenzyme QH and nicotinamide at 3465 cm$^{-1}$, 3170 cm$^{-1}$ and 1697 cm$^{-1}$, indicating that the coenzyme QH composition comprises the co-crystal of coenzyme QH and nicotinamide. At the same time, there was a characteristic peak of nicotinamide at 3368 cm$^{-1}$, indicating that the composition was composed of nicotinamide and the co-crystal of coenzyme QH and nicotinamide.

Example 9 (Comparison of the Stabilities of Coenzyme QH Itself and the Coenzyme QH Co-Crystal of the Present Invention)

The coenzyme QH obtained in Example 1 and the co-crystal of coenzyme QH and nicotinamide or the coenzyme QH compositions obtained in Examples 4-6 were used.

The coenzyme QH obtained in Example 1 and the co-crystals comprising coenzyme QH and nicotinamide obtained in Examples 4-6 were compared in terms of stability. The coenzyme QH obtained in Example 1 and the coenzyme QH co-crystals obtained in Examples 4-6 were open stored away from light under the conditions of 25° C./60% relative humidity. The weight ratio of coenzyme QH and oxidized coenzyme Q10 was analyzed by HPLC. The results are shown in Table 1.

TABLE 1

| | Weight ratio of coenzyme QH and oxidized coenzyme Q10 | | | |
|---|---|---|---|---|
| Number of days | Coenzyme QH obtained in Example 1 | Co-crystal obtained in Example 4 | Co-crystal obtained in Example 5 | Coenzyme QH composition obtained in Example 6 |
| Day 0 | 99.2.0/0.8 | 97.9/2.1 | 98.3/1.7 | 98.4/1.6 |
| Day 3 | 91.4/8.6 | 97.5/2.5 | 98.5/1.5 | 98.4/1.6 |
| Day 7 | 85.9/14.1 | 96.3/3.7 | 98.3/1.7 | 97.9/2.1 |
| Day 14 | 71.2/28.8 | 90.8/9.2 | 98.1/1.9 | 94.3/5.7 |

As shown in the above results, compared with the coenzyme QH prepared in Example 1, the coenzyme QH composition or co-crystal disclosed in the present invention has more excellent stability, and can still remain stable for a long time without deliberately taking protective measures against oxygen, indicating that the coenzyme QH co-crystal of the present invention had significantly improved stability compared with the coenzyme QH itself.

Comparative Example 1

0.244 g of nicotinic acid and 1.72 g of the coenzyme QH obtained in Example 1 were added to a ball mill jar, and 1 ml of ethanol was added thereto. The ball milling was performed for 2 hours. The solid was dried in a vacuum oven at room temperature for 12 hours to obtain a yellow powder.

Figure 14:
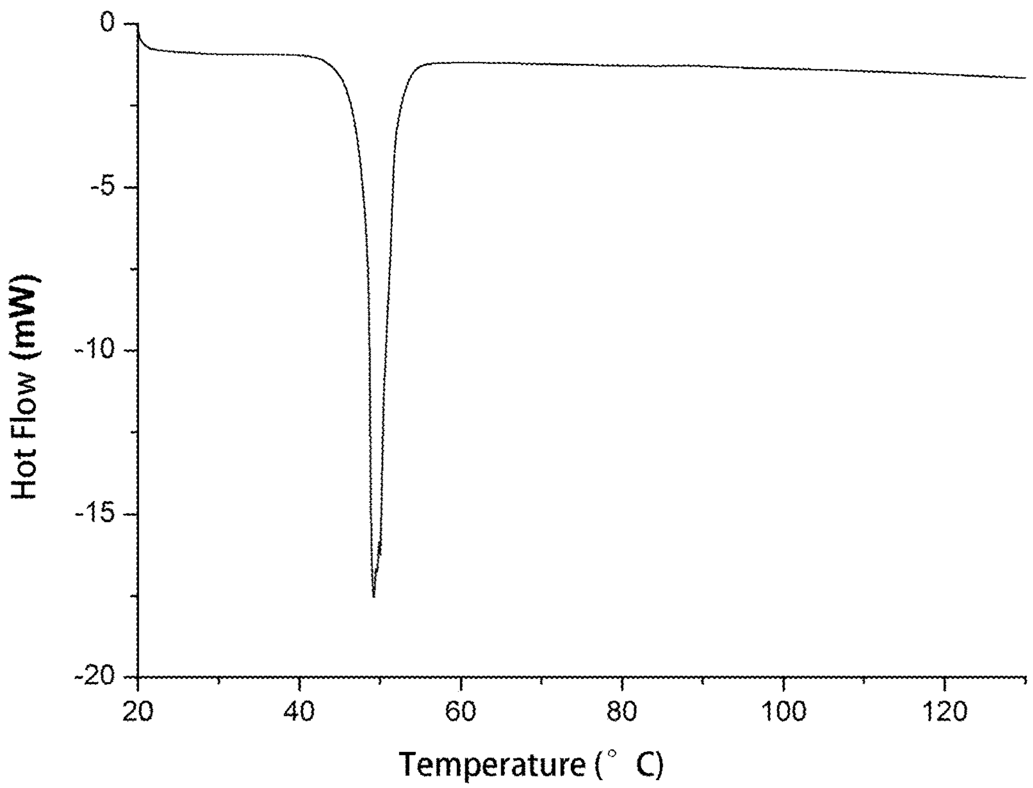
FIG. 14 is a differential scanning calorimetry (DSC) pattern of comparative example 1 provided by the present invention.

This powder was detected by differential scanning calorimetry (DSC), and the results are shown in FIG. 14. Compared with the QH itself, there was no significant difference in melting point.

Comparative Example 2

0.752 g of riboflavin and 1.72 g of the coenzyme QH obtained in Example 1 were added to a ball mill jar, and 1 ml of ethanol was added thereto. The ball milling was performed for 2 hours. The solid was dried in a vacuum oven at room temperature for 12 hours to obtain a yellow powder.

Figure 15:
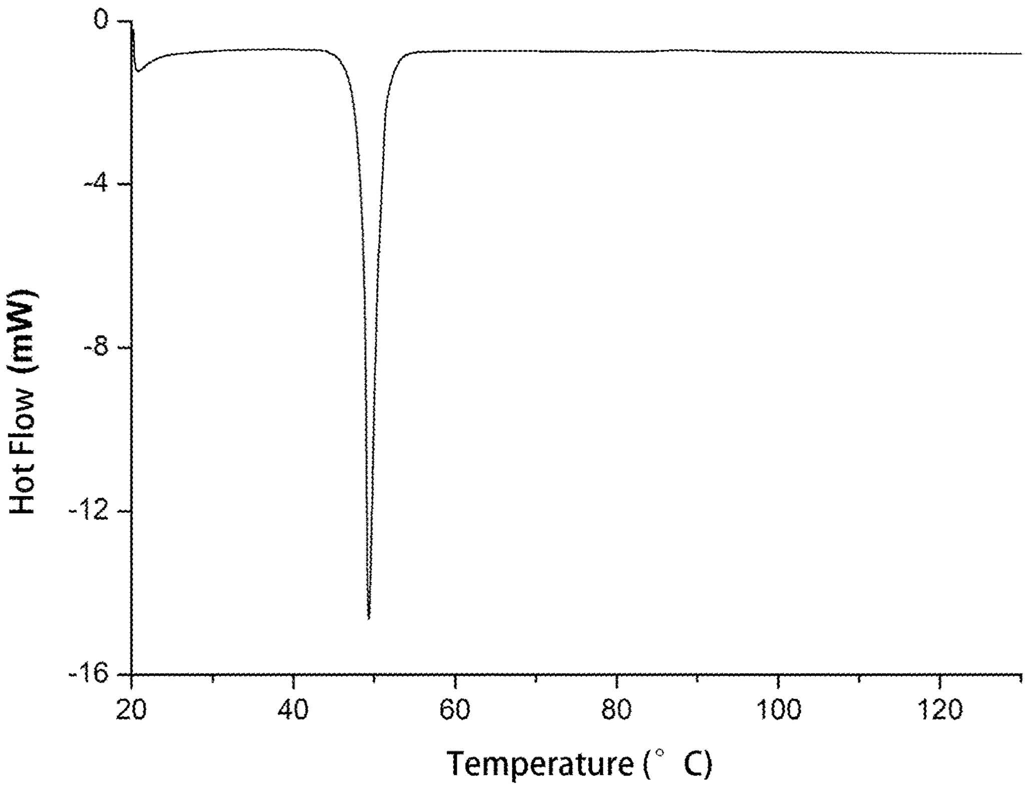
FIG. 15 is a differential scanning calorimetry (DSC) pattern of comparative example 2 provided by the present invention.

This powder was detected by differential scanning calorimetry (DSC), and the results are shown in FIG. 15. Compared with the QH itself, there was no significant difference in melting point.

Comparative Example 3

0.477 g of calcium pantothenate and 1.72 g of the coenzyme QH obtained in Example 1 were added to a ball mill jar, and 1 ml of ethanol was added thereto. The ball milling was performed for 2 hours. The solid was dried in a vacuum oven at room temperature for 12 hours to obtain an off-white powder.

Figure 16:
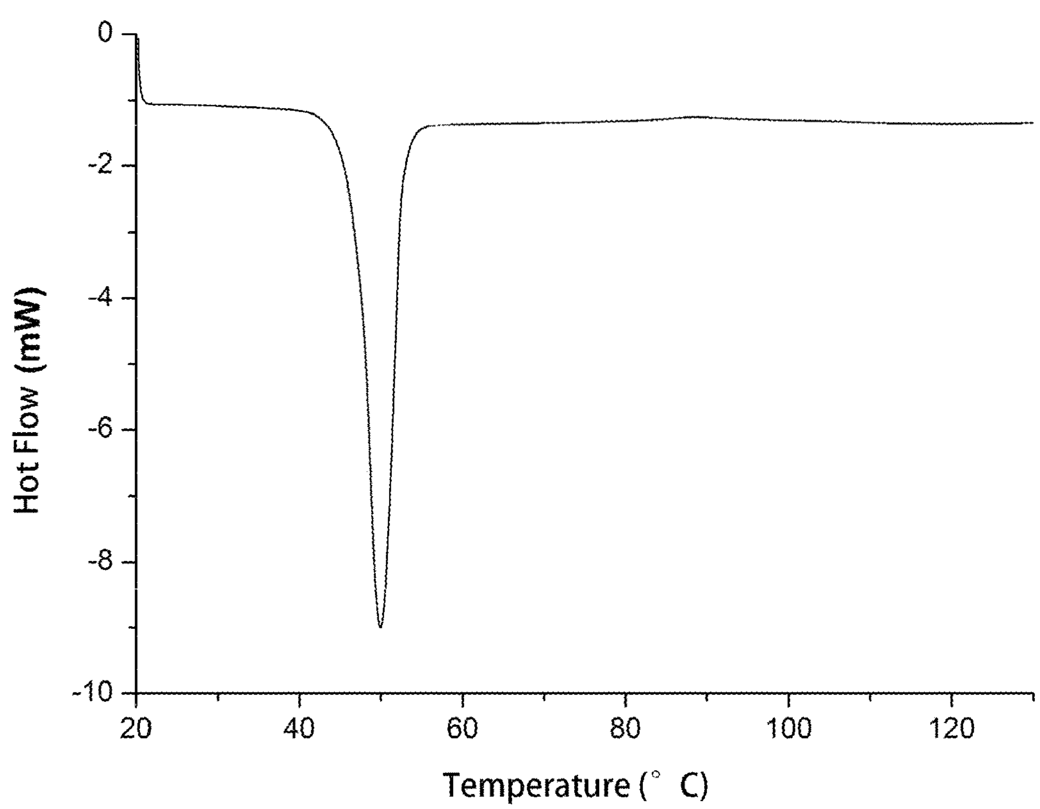
FIG. 16 is a differential scanning calorimetry (DSC) pattern of comparative example 3 provided by the present invention.

This powder was detected by differential scanning calorimetry (DSC), and the results are shown in FIG. 16. Compared with the QH itself, there was no significant difference in melting point.

Comparative Example 4

0.882 g of folic acid and 1.72 g of the coenzyme QH obtained in Example 1 were added to a ball mill jar, and 1 ml of ethanol was added thereto. The ball milling was performed for 2 hours. The solid was dried in a vacuum oven at room temperature for 12 hours to obtain a yellow powder.

Figure 17:
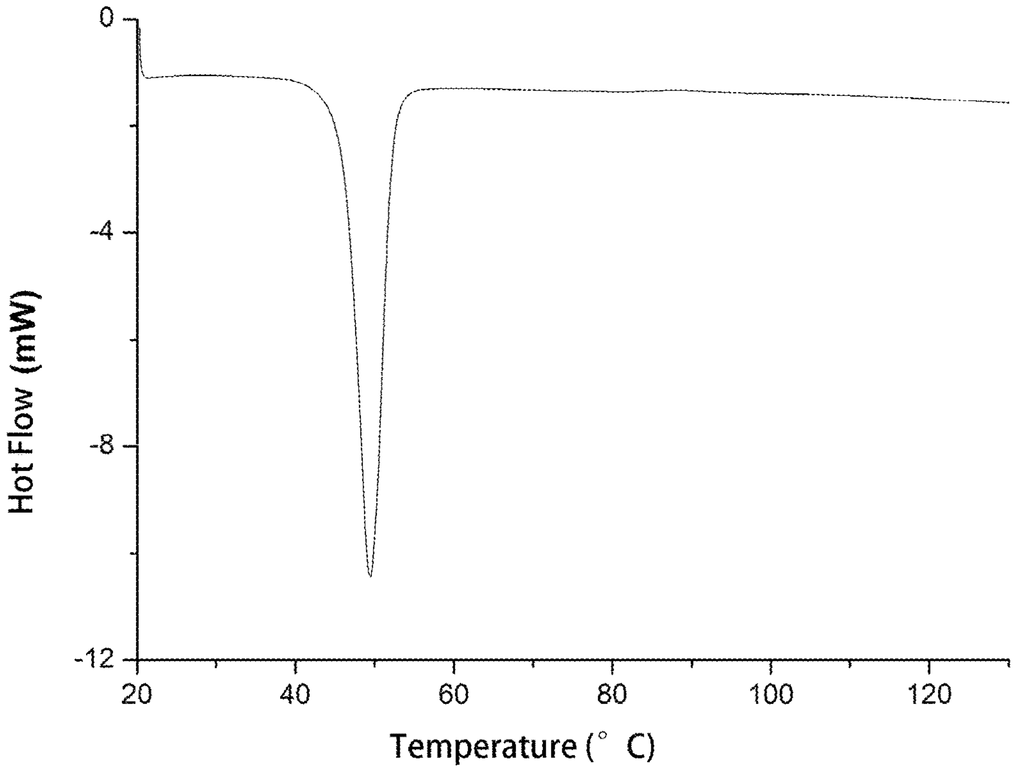
FIG. 17 is a differential scanning calorimetry (DSC) pattern of comparative example 4 provided by the present invention.

This powder was detected by differential scanning calorimetry (DSC), and the results are shown in FIG. 17. Compared with the QH itself, there was no significant difference in melting point.

Comparative Example 5

0.352 g of ascorbic acid and 1.72 g of the coenzyme QH obtained in Example 1 were added to a ball mill jar, and 1 ml of ethanol was added thereto. The ball milling was performed for 2 hours. The solid was dried in a vacuum oven at room temperature for 12 hours to obtain an off-white powder.

Figure 18:
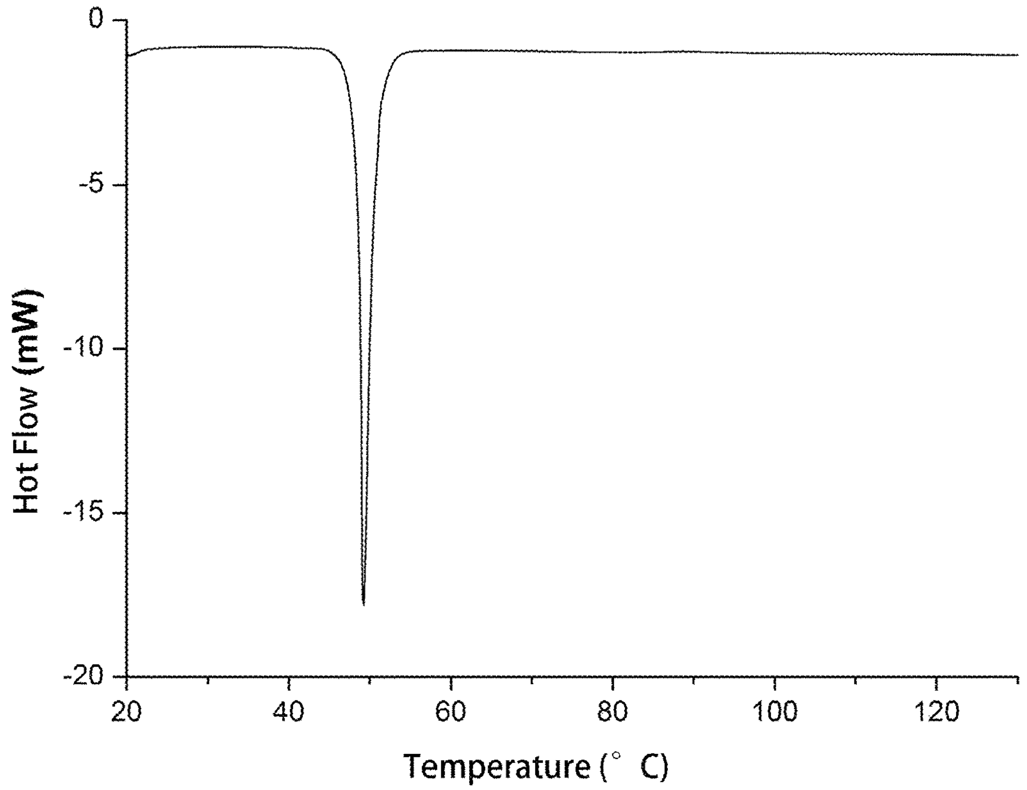
FIG. 18 is a differential scanning calorimetry (DSC) pattern of comparative example 5 provided by the present invention.

This powder was detected by differential scanning calorimetry (DSC), and the results are shown in FIG. 18. Compared with the QH itself, there was no significant difference in melting point.

The above results indicate that none of niacin, riboflavin, calcium pantothenate, folic acid, and ascorbic acid could form a co-crystal with coenzyme QH to improve the stability of coenzyme QH.

What is claimed is:

1. A co-crystal of coenzyme QH and nicotinamide, wherein the stoichiometric ratio of coenzyme QH to nicotinamide is 1:1 in the co-crystal, and wherein the co-crystal has an X-ray powder diffraction pattern having characteristic peaks at 2θ angles of 4.3°±0.2°, 5.7°±0.2°, 17.1°±0.2°, 17.9°±0.2°, 18.9°±0.2°, 19.8°±0.2°, 20.8°±0.2° and 23.1°±0.2°.

2. The co-crystal of coenzyme QH and nicotinamide according to claim 1, wherein the co-crystal has a differential scanning calorimetry pattern having a characteristic endothermic peak at 57±2° C., as determined by differential scanning calorimetry with a temperature increase rate of 10° C./min.

3. The co-crystal of coenzyme QH and nicotinamide according to claim 1, wherein the co-crystal has an infrared spectrum having characteristic peaks at 3465 $cm^{-1}$, 3170 $cm^{-1}$ and 1697 $cm^{-1}$.

4. The co-crystal of coenzyme QH and nicotinamide according to claim 1, wherein the co-crystal has an X-ray powder diffraction pattern having characteristic peaks at 2θ angles of 8.4°±0.2°, 9.9°±0.2°, 18.6°±0.2°, 19.1°±0.2°, 27.8°±0.2° and 30.3°±0.2°.

5. The co-crystal of coenzyme QH and nicotinamide according to claim 1, wherein the co-crystal has an infrared spectrum having characteristic peaks at 2964 $cm^{-1}$, , 2945 $cm^{-1}$, 2907 $cm^{-1}$, 2847 $cm^{-1}$, 1664 $cm^{-1}$, 1607 $cm^{-1}$, 1445 $cm^{-1}$, 1422 $cm^{-1}$, 1384 $cm^{-1}$, 1280 $cm^{-1}$, 1261 $cm^{-1}$, 1197 $cm^{-1}$, 1164 $cm^{-1}$, 1149 $cm^{-1}$, 1109 $cm^{-1}$, 1009 $cm^{-1}$, 907 $cm^{-1}$, 877 $cm^{-1}$, 795 $cm^{-1}$, 751 $cm^{-1}$, 599 $cm^{-1}$ and 475 $cm^{-1}$.

6. A method for preparing the co-crystal of coenzyme QH and nicotinamide according to claim 1, comprising:

subjecting coenzyme QH and nicotinamide to ball milling in a solvent for 10 minutes or more to obtain a solid, wherein the solvent is one or more selected from the group consisting of water, methanol, ethanol, isopropanol, ethyl acetate, isopropyl acetate, acetone, methyl tert-butyl ether, n-hexane and n-heptane; and drying the obtained solid to obtain the co-crystal of coenzyme QH and nicotinamide.

7. A method for preparing the co-crystal of coenzyme QH and nicotinamide according to claim 1, comprising:

recrystallizing coenzyme QH and nicotinamide in a solvent to obtain a precipitate, wherein the solvent is one or more selected from the group consisting of water, methanol, ethanol, isopropanol, ethyl acetate, isopropyl acetate, acetone, methyl tert-butyl ether, n-hexane and n-heptane; and drying the precipitate to obtain the co-crystal of coenzyme QH and nicotinamide.

* * * * *